: US 10,465,283 B2
(45) Date of Patent: Nov. 5, 2019

(12) United States Patent
Harada et al.

(54) ORGANOPLATINUM COMPOUND FOR USE IN THE CHEMICAL DEPOSITION OF PLATINUM COMPOUND THIN FILMS

(71) Applicant: TANAKA KIKINZOKU KOGYO K.K., Chiyoda-ku, Tokyo (JP)

(72) Inventors: Ryosuke Harada, Tsukuba (JP); Toshiyuki Shigetomi, Tsukuba (JP); Kazuharu Suzuki, Tsukuba (JP); Shunichi Nabeya, Tsukuba (JP); Akiko Kumakura, Tsukuba (JP); Rumi Kobayashi, Tsukuba (JP); Takayuki Sone, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 13 days.

(21) Appl. No.: 15/558,057

(22) PCT Filed: May 9, 2016

(86) PCT No.: PCT/JP2016/063692
§ 371 (c)(1),
(2) Date: Sep. 13, 2017

(87) PCT Pub. No.: WO2016/181915
PCT Pub. Date: Nov. 17, 2016

(65) Prior Publication Data
US 2018/0066357 A1 Mar. 8, 2018

(30) Foreign Application Priority Data
May 12, 2015 (JP) ................................ 2015-096975

(51) Int. Cl.
| C07F 15/00 | (2006.01) |
| C23C 16/18 | (2006.01) |
| C07C 211/21 | (2006.01) |
| H01L 21/285 | (2006.01) |
| C23C 16/46 | (2006.01) |
| H01L 49/02 | (2006.01) |

(52) U.S. Cl.
CPC ............ *C23C 16/18* (2013.01); *C07C 211/21* (2013.01); *C07F 15/00* (2013.01); *C07F 15/0086* (2013.01); *C23C 16/46* (2013.01); *H01L 21/285* (2013.01); *H01L 28/65* (2013.01)

(58) Field of Classification Search
CPC ..... C07F 15/0086; C23C 16/18; H01L 28/65; H01L 21/28568
See application file for complete search history.

(56) References Cited

U.S. PATENT DOCUMENTS

| 4,614,811 A * | 9/1986 | Gandolfi | C07F 15/0093 556/137 |
| 4,870,062 A * | 9/1989 | Kurono | C07F 15/0093 514/63 |
| 5,510,437 A * | 4/1996 | Shimada | B01J 31/1691 526/241 |
| 2002/0127412 A1 * | 9/2002 | Leman | B01J 31/1608 428/447 |
| 2009/0023830 A1 * | 1/2009 | Imai | C08F 2/48 522/74 |
| 2009/0149417 A1 * | 6/2009 | Ossovskaya | A61K 31/282 514/49 |
| 2011/0111556 A1 | 5/2011 | Chen et al. | |
| 2013/0344243 A1 * | 12/2013 | Suzuki | C07F 15/0086 427/252 |

(Continued)

FOREIGN PATENT DOCUMENTS

| EP | 0288002 A2 * | 4/1988 | ............ C07F 15/00 |
| EP | 1083161 A1 * | 3/2001 | ............ C07C 17/02 |

(Continued)

OTHER PUBLICATIONS

Ebert, K.H., et al., "Organoplatinunn compounds: VI1. Trimethylplatinum thiomethylate and trimethylplatinum iodide. The crystal structures of [(CH3)3PtS(CH3)]4 and [(CH3)3PtI]4 0.5Ch3I2". Journal of Organometallic Chemistry, 559 (1998) 203-207.*

(Continued)

*Primary Examiner* — Bret P Chen
(74) *Attorney, Agent, or Firm* — Orrick, Herrington & Sutcliffe LLP; Joseph A. Calvaruso; K. Patrick Herman (57) ABSTRACT

An organoplatinum compound with the following formula for use as a raw material in the chemical deposition of platinum compound thin films. In the formula, n is 1 or more and 5 or less. Each of substituents R1 to R5 on the alkenyl amine is a hydrogen atom, an alkyl group or the like and has a carbon number of 4 or less. Each of alkyl anions R6 and R7 is an alkyl group having a carbon number of 1 or more and 3 or less. The vapor pressure of the organoplatinum compound is high enough to allow for the manufacturing of a platinum thin film at low temperature. It also has moderate thermal stability.

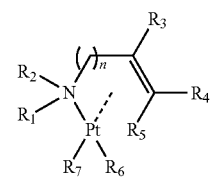

11 Claims, 4 Drawing Sheets

(56) References Cited

U.S. PATENT DOCUMENTS

2015/0030772 A1* 1/2015 Saito ................. C23C 16/18
                                                          427/252

FOREIGN PATENT DOCUMENTS

| JP | 59-139360 | * | 8/1984 |
|----|-----------|---|--------|
| JP | 7-247362 | * | 9/1995 |
| JP | 8-157490 | * | 6/1996 |
| JP | 10-1492 | * | 1/1998 |
| JP | 11-292889 A | | 10/1999 |
| JP | 2001-504159 A | | 3/2001 |
| WO | WO 2012/144455 A1 | | 10/2012 |

OTHER PUBLICATIONS

Klein, Axel, "Stayin' Alive—Organoplatinum Complexes". Inorganics 2015, 3, 155-159.*
Clark, H.C., et al., "Reactions of (t-1,5-cyclooctadiene) organoplatinum(II) compounds and the synthesis of perfluoroalkylplatinum complexes". Journal of Organometallic Chemistry, vol. 59, Oct. 1, 1973, pp. 411-428.*
Ebert, K.H., et al., "Organoplatinunn compounds: VI Trimethylplatinum thiomethylate and trimethylplatinum iodide. The crystal structures of [(Ch3)3PtS(CH3))]4 and [(CH3)3PtI]4'0.5Ch3I2". Journal of Organometallic Chemistry, vol. 559 (1998) 203-207.*
Baukova, T.V., et al., "Synthesis, structure, and properties of organoplatinum(II) derivatives of diphenyl ether". Russian Chemical Bulletin, vol. 43, No. 10, Oct. 1994, pp. 1719-1725.*
PCT, International Search Report for PCT/JP2016/063692, dated Jun. 7, 2016.

* cited by examiner

ORGANOPLATINUM COMPOUND FOR USE IN THE CHEMICAL DEPOSITION OF PLATINUM COMPOUND THIN FILMS

TECHNICAL FIELD

The present invention relates to a raw material for chemical deposition composed of an organoplatinum compound for manufacturing a platinum thin film or a platinum compound thin film by a chemical deposition method, such as a CVD method or an ALD method. In particular, the present invention relates to a raw material for chemical deposition capable of forming a platinum thin film and the like even at low temperature of not more than 200° C., with moderate thermal stability.

BACKGROUND ART

A stereoscopic Ni—Pt silicide electrode having a three-dimensional structure is known as an electrode material of a field-effect transistor (FET) that is built in an integrated circuit. In the manufacturing of the Ni—Pt silicide electrode, a chemical deposition method, such as a CVD method, is utilized when a Pt thin film and a Ni thin film are formed on previously manufactured Si having a steric structure. Further, also in a gate electrode of an FET, a chemical deposition method, such as a CVD method capable of forming a film at low temperature, is suitable in achieving size reduction/high performance.

Many compounds are conventionally known as raw materials for manufacturing a platinum thin film or a platinum compound thin film by the CVD method. For example, bis(acetylacetonate)platinum (II) complex (PTL 1), (cyclopentadienyl)trimethylplatinum (IV)) complex (PTL 2) and the like are mentioned. Required performance of these raw materials for CVD generally include capability of deposition at low temperature because of high vapor pressure and low decomposition temperature.

[Chemical Formula 1]

Bis(acetylacetonate)platinum (II)   (Cyclopentadienyl)trimethylplatinum (IV))

In response to such demand, (1,5-hexadiene)dimethylplatinum (II) or the like is proposed as a compound in which hexadiene (derivative) and an alkyl anion are coordinated to divalent platinum in order to provide a raw material for CVD that is thermally decomposed easily even at low temperature (PTL 3).

[Chemical Formula 2]

CITATION LIST

Patent Literature

PTL 1: Published Japanese translation of PCT patent application No. 2001-504159
PTL 2: Japanese Patent Laid-Open Heisei No. 11-292889
PTL 3: International Publication No. WO 2012/144455 Pamphlet

SUMMARY OF INVENTION

Technical Problem

Raw materials in the past as described above possess a part of required characteristics for a CVD compound, but do not possess all the required characteristics in a well-balanced manner. For example, platinum compounds in PTL 1 and PTL 2 have high thermal stability but are difficult to deposit at low temperature. The platinum compound in PTL 3 is thermally decomposed easily and excellent in low temperature deposition properties, but the compound is infrequently decomposed in storage or in vaporization stage before deposition, and there is a room for improvement about thermal stability. As described above, with respect to low temperature deposition properties in a deposition stage and thermal stability before the deposition stage, such as during storage, when one is possessed, the other is difficult to be realized and there is such a tendency that it is difficult to provide a compound that possesses both characteristics in a balanced manner.

Against such a background, the present invention provides a raw material that possesses characteristics required for a CVD compound in a well-balanced manner, that is, a platinum compound for CVD that is capable of forming a film deposition at low temperature and has sufficient thermal stability without thermal decomposition in a vaporization stage.

Solution to Problem

The present invention that solves above-described problems relates to a raw material for chemical deposition for manufacturing a platinum thin film or a platinum compound thin film by a chemical deposition method, the raw material including an organoplatinum compound in which an alkenyl amine and an alkyl anion that are coordinated to a divalent platinum as shown by a formula below,

[Chemical Formula 3]

(wherein n is 1 or more and 5 or less; each of $R_1$ to $R_5$ represents any one of a hydrogen atom, an alkyl group, an alkenyl group, an alkynyl group, an amino group, an imino group, a cyano group and an isocyano group, and each has a carbon number of not more than 4; and each of $R_6$ and $R_7$ represents an alkyl group having a carbon number of 1 or more and 3 or less.)

In the present inventive raw material for chemical deposition, an alkenyl amine and two alkyl anions are coordinated as ligands of divalent platinum as shown below. The present inventors conceived the platinum compound on the basis of the following reason with respect to respective constitutions of a central metal and ligands to be coordinated to the metal.

[Chemical Formula 4]

The "alkenyl amine" in the present invention is a ligand composed of an amine and a hydrocarbon having a double bond. The ligand including an amine is thus applied because the inventors found that thermal stability and vapor pressure of a platinum compound tend to vary easily by the introduction of an amine. Because a bonding site between a C=C double bond and a platinum compound is separated easily in a ligand not having an amine (diene) as shown below, vapor pressure is high and deposition at low temperature becomes easy, but thermal stability tends to deteriorate and handling is difficult. In contrast, a ligand having two amines (diamine) has high thermal stability, but has low vapor pressure and tends to make film deposition at low temperature difficult. Therefore, a ligand including an amine is applied in the present invention in consideration of a balance between the thermal stability and the vapor pressure. Further, selection of an alkenyl amine having a small molecular weight and a low boiling point can result in a ligand that evaporates easily after decomposition and is hard to remain in the metal film as an impurity.

[Chemical Formula 5]

Suitable setting of a molecular weight of an alkyl anion that is another ligand can also control the vapor pressure of a complex to some degree. An alkyl anion whose molecular weight is controlled is emitted as a low boiling point hydrocarbon by performing film deposition in a reducing atmosphere, such as hydrogen gas, and causing the complex to decompose. Consequently, an alkyl anion with a controlled molecular weight is hard to become a residual impurity in a deposited metal film and is suitable as a ligand for causing pure metal to be emitted.

Furthermore, with respect to platinum to be a central metal, most of platinum complexes with platinum having positive di- or tetra-charges as a central metal are stable, and the present inventors prefer a divalent platinum complex having moderate stability because easy handling of the compound in the processes of synthesis/purification/storage is also important. On the basis of the above reason, an alkenyl amine and an alkyl anion are coordinated as ligands to divalent platinum in the present inventive raw material.

Details of suitable substituents and the like will be described about the above-mentioned platinum ligand.

The alkenyl amine has n of 1 or more and 5 or less, and concrete compounds include propenyl amine or derivatives of the propenyl amine (n=1), butenyl amine or derivatives of the butenyl amine (n=2), pentenyl amine or derivatives of the pentenyl amine (n=3), hexenyl amine or derivatives of the hexenyl amine (n=4), and heptenyl amine or derivatives of the heptenyl amine (n=5). n is preferably 1 or more and 4 or less. The application of a comparatively small alkyl group can suppress the reduction of vapor pressure with the increase of a molecular weight. Further, since a longer carbon chain tends to decrease the stability of a platinum complex, synthesis/handling of a platinum complex become difficult when a long chain alkene having n exceeding 5 is applied.

Particularly preferable is 2 or 3 as n, and suitable is a raw material for chemical deposition composed of organoplatinum compounds that have any of a butenyl amine or derivatives of the butenyl amine and a pentenyl amine or derivatives of the pentenyl amine as a ligand, as shown by formulae below,

[Chemical Formula 6]

(wherein each of $R_1$ to $R_5$ represents any one of a hydrogen atom, an alkyl group, an alkenyl group, an alkynyl group, an amino group, an imino group, a cyano group and an isocyano group, and has a carbon number of 4 or less. Each of $R_6$ and $R_7$ represents an alkyl group having a carbon number of 1 or more and 3 or less.)

Each of the substituents $R_1$ and $R_2$ on a nitrogen atom in an alkenyl amine is any one of a hydrogen atom, an alkyl group, an alkenyl group, an alkynyl group, an amino group, an imino group, a cyano group and an isocyano group, and has a carbon number of 4 or less. Each of the substituents $R_1$ and $R_2$ is preferably any one of a hydrogen atom, a methyl group, an ethyl group and a propyl group, and is particularly preferably a methyl group or an ethyl group. Any of a linear chain (n-) and branched chains (iso-, sec-, tert-) that are structural isomers may be used when an alkyl group having a carbon number of 3 or more is to be used, but a linear chain is preferable.

The substituent $R_3$ is a hydrogen atom, an alkyl group, an alkenyl group, an alkynyl group, an amino group, an imino group, a cyano group or an isocyano group, and has a carbon number of 1 or more and 4 or less. The substituent $R_3$ is preferably a hydrogen atom, a methyl group or an ethyl group, and is particularly preferably a hydrogen atom. Any of a linear chain (n-) and branched chains (iso-, sec-, tert-) that are structural isomers may be used when an alkyl group having a carbon number of 3 or more is to be used, but a linear chain is preferable.

Each of the substituents $R_4$ and $R_5$ is any one of a hydrogen atom, an alkyl group, an alkenyl group, an alkynyl group, an amino group, an imino group, a cyano group and an isocyano group, and has a carbon number of 4 or less. Each of the substituents $R_4$ and $R_5$ is preferably a hydrogen atom or a methyl group, and is particularly preferably a hydrogen atom. Any of a linear chain (n-) and branched chains (iso-, sec-, tert-) that are structural isomers may be used when an alkyl group having a carbon number of 3 or more is to be used, but a linear chain is preferable.

Each of two alkyl anions $R_6$ and $R_7$ is preferably an alkyl group having a carbon number of 1 or more and 3 or less, that is, any one of a methyl group, an ethyl group and an n-propyl group. These alkyl anions have a small molecular weight, and therefore can suppress decrease of vapor pressure with the increase of molecular weight also when a complex is to be formed. Further, the stability of a platinum complex tends to decrease as the carbon chain of an alkyl group becomes long, and therefore synthesis/handling of a complex become difficult when a long chain alkyl group having a carbon number of 4 or more is used as a ligand. A group that is particularly preferable as $R_6$ and $R_7$ is a methyl group. The methyl group becomes methane having a low boiling point (boiling point: −162° C.) after the decomposition of a complex, and therefore can be emitted without leaving an impurity in a metal thin film to be formed.

Kinds of organoplatinum compounds that are suitable for the raw material for chemical deposition of the present invention are concretely exemplified below.

[Chemical Formula 7]

The above-described raw material for chemical deposition of the present invention can be manufactured with a platinum salt used as a starting material, by adding and causing the platinum salt that is the starting material to react with an alkenyl amine. Meanwhile, for example, (1,5-hexadiene)dimethylplatinum or the like can be used as a platinum salt.

The present inventive raw material for chemical deposition is useful for forming a platinum thin film by a CVD method. In the method for forming a thin film, a raw material composed of an organoplatinum compound is vaporized to be a reaction gas, the reaction gas is introduced to a substrate surface, and the organoplatinum compound is decomposed to precipitate platinum, in which the present inventive organoplatinum compound is used as a raw material.

A reducing atmosphere is preferable as a reaction atmosphere in forming a platinum film. The raw material of the present invention tends to show good low-temperature film deposition properties particularly in a reducing atmosphere. Further, a reducing atmosphere also suppresses oxidization of a nickel thin film that is formed together with platinum in a stereoscopic electrode of an FET. As a reducing atmosphere, introduction of hydrogen or ammonia as a reaction gas is preferable, and hydrogen is particularly preferable.

The present invention aims at setting film deposition temperature on a low-temperature side. From the viewpoint, heating temperature for a deposition reaction is preferably 100° C. to 350° C. Because progress of a deposition reaction is difficult and acquisition of a necessary film thickness is difficult when the heating temperature is less than 100° C. Further because, when the heating temperature exceeds 350° C., it becomes difficult not only to form a uniform thin film on a stereoscopic electrode but also to maintain performance of an FET element.

Advantageous Effects of Invention

As described above, the platinum complex of the present inventive raw material for chemical deposition has high vapor pressure to make possible the manufacturing of a platinum thin film at low temperature and also has moderate thermal stability. Meanwhile, the present inventive raw material may also be applied to chemical deposition methods, such as an atomic layer deposition method (ALD method), in addition to a CVD method.

DESCRIPTION OF EMBODIMENTS

Hereinafter, the best embodiment in the present invention will be described.

First Embodiment

Five kinds of platinum complexes were synthesized in the present embodiment. Physical properties of the synthesized platinum complexes were evaluated, and film deposition tests were performed as raw materials for chemical deposition.

[Chemical Formula 8]

Example 1

Example 2

Example 3

Example 4

Example 5

Example 1

As a raw material for chemical deposition, manufactured was a platinum complex (dimethyl(N,N-dimethyl-3-butene-1-amine)platinum) in which N,N-dimethyl-3-butene-1-amine and two methyl groups being alkyl anions were coordinated. The synthesis reaction formula is as follows. Hereinafter, the manufacturing process will be described in detail.

[Chemical Formula 9]

Each of 0.75 g (7.5 mmol) of N,N-dimethyl-3-butene-1-amine and 1.54 g (5.0 mmol) of (1,4-hexadiene)dimethylplatinum was added in this order to a flask containing 50 ml of hexane, and then the mixture was stirred for 20 hours at room temperature. After the end of the reaction, the reaction product was concentrated to give a white solid. The obtained white solid was sublimated and purified to give 1.55 g (4.8 mmol) of dimethyl(N,N-dimethyl-3-butene-1-amine)platinum that was the target (yield: 96%, melting point: 76° C.).

Example 2

As a raw material for chemical deposition, manufactured was a platinum complex (dimethyl(N-ethyl-N-methyl-3-butene-1-amine)dimethylplatinum) in which N-ethyl-N-methyl-3-butene-1-amine and two methyl groups being alkyl anions were coordinated. The synthesis reaction formula is as follows. Hereinafter, the manufacturing process will be described in detail.

[Chemical Formula 10]

Each of 0.62 g (5.5 mmol) of N-ethyl-N-methyl-3-butene-1-amine and 1.54 g (5.0 mmol) of (1,4-hexadiene)dimethylplatinum was added in this order to a flask containing 50 ml of hexane, and then the mixture was stirred for 20 hours at room temperature. After the end of the reaction, the reaction product was concentrated to give a white solid. The obtained white solid was sublimated and purified to give 1.53 g (4.3 mmol) of dimethyl(N,N-diethyl-3-butene-1-amine)dimethylplatinum that was the target (yield: 86%, melting point: 51° C.).

Example 3

As a raw material for chemical deposition, manufactured was a platinum complex ((N,N-diethyl-3-butene-1-amine)dimethylplatinum) in which N,N-diethyl-3-butene-1-amine and two methyl groups being alkyl anions were coordinated. The synthesis reaction formula is as follows. Hereinafter, the manufacturing process will be described in detail.

[Chemical Formula 11]

Each of 0.70 g (5.5 mmol) of N,N-diethyl-3-butene-1-amine and 1.54 g (5.0 mmol) of (1,4-hexadiene)dimethylplatinum was added in this order to a flask containing 50 ml of hexane, and then the mixture was stirred for 20 hours at room temperature. After the end of the reaction, the reaction product was concentrated to give a white solid. The obtained white solid was sublimated and purified to give 1.53 g (4.3 mmol) of dimethyl(N,N-diethyl-3-butene-1-amine)dimethylplatinum that was the target (yield: 87%, melting point: 58° C.).

Example 4

As a raw material for chemical deposition, manufactured was a platinum complex ((methyl)(N,N-dimethyl-3-butene-1-amine)(propyl)platinum) in which N,N-dimethyl-3-butene-1-amine and a methyl group and a propyl group being alkyl anions were coordinated. The synthesis reaction formula is as follows. Hereinafter, the manufacturing process will be described in detail.

[Chemical Formula 12]

Each of 0.55 g (5.5 mmol) of N,N-dimethyl-3-butene-1-amine and 1.54 g (5.0 mmol) of (1,4-hexadiene)dimethylplatinum was added in this order to a flask containing 50 ml of hexane, and then the mixture was refluxed for 20 hours. After the end of the reaction, generation of 0.30 g (0.85 mmol) of (methyl)(N,N-dimethyl-3-butene-1-amine)(propyl)platinum that was the target was confirmed.

Example 5

As a raw material for chemical deposition, manufactured was a platinum complex (dimethyl(N,N-dimethyl-4-pentene-1-amine) in which N,N-dimethyl-4-pentene-1-amine and two methyl groups being alkyl anions were coordinated. The synthesis reaction formula is as follows. Hereinafter, the manufacturing process will be described in detail.

[Chemical Formula 13]

Each of 0.62 g (5.5 mmol) of N,N-dimethyl-4-pentene-1-amine and 1.54 g (5.0 mmol) of (1,4-hexadiene)dimethylplatinum was added in this order to a flask containing 50 ml of hexane, and then the mixture was stirred for 20 hours at room temperature. After the end of the reaction, generation of 0.42 g (1.25 mmol) of dimethyl(N,N-dimethyl-4-pentene-1-amine)platinum that was the target was confirmed.

Evaluation of Physical Properties of Platinum Complexes:

Evaluation of physical properties by TG-DTA was performed on platinum complexes manufactured in Examples 1 to 3. In the analysis, changes in heat quantity and weight of a sample were observed when a platinum complex sample (5 mg) was heated from room temperature to 450° C. that was a range of measurement temperature at a temperature rising rate of 5° C./min under a nitrogen atmosphere with TG-DTA2000SA manufactured by BRUKER Corporation. Results are shown in FIG. 1.

Figure 1:
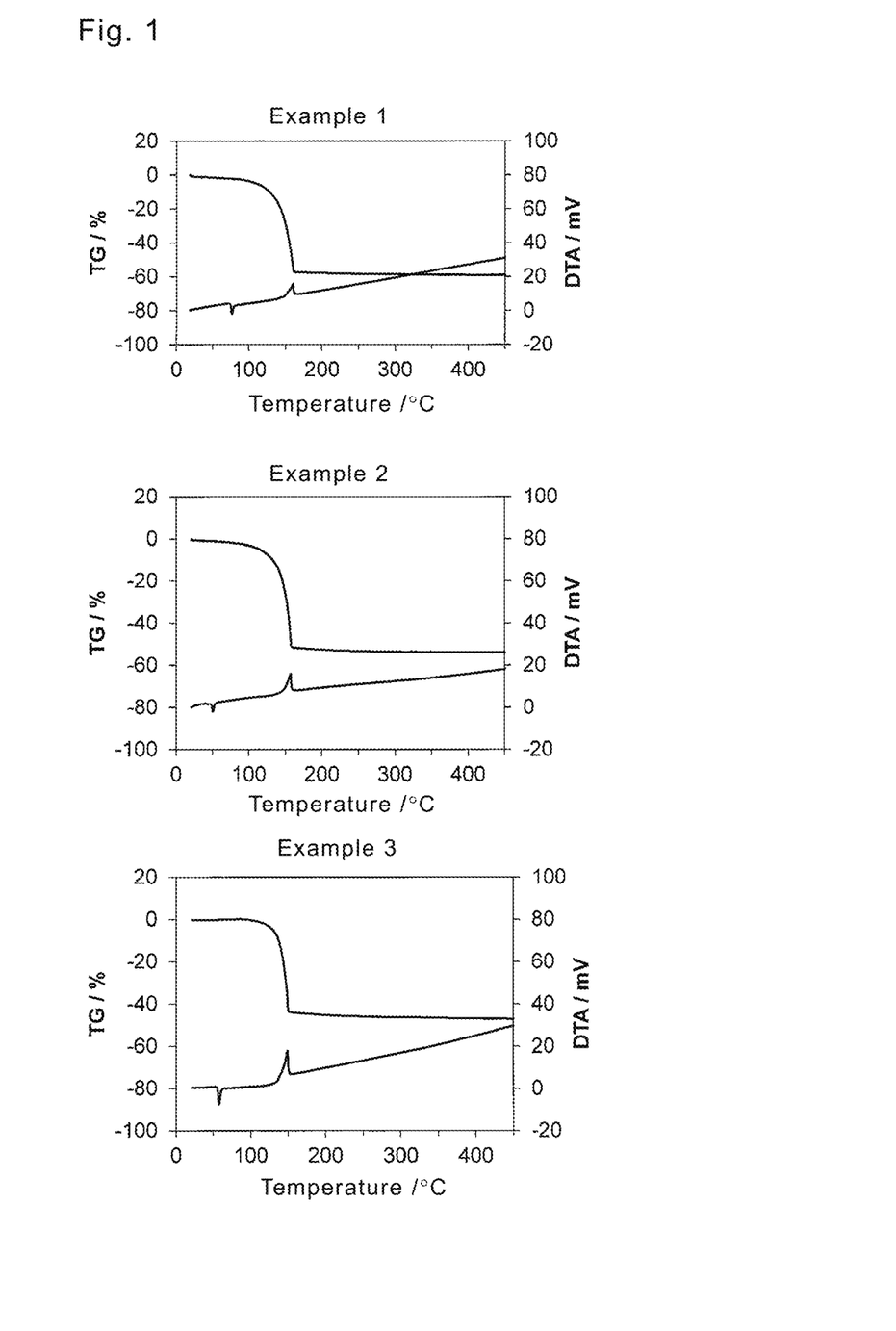
FIG. 1 shows a TG-DTA curve of a platinum complex in a first embodiment.

From the result of DTA in FIG. 1, the platinum complex in Example 1 had a melting point of about 75° C. from a concave peak and a decomposition temperature of about 150° C. from a convex peak, and had sufficient thermal stability for handling for deposition. Further, about 30% of the platinum complex had been vaporized until the decomposition temperature from weight decrease prior to the decomposition temperature and residue weight after the heating, from the result of TG. From the above, it was shown that both decomposition and vaporization were generated, deposition at comparatively low temperatures was possible and vaporization in deposition also tended to progress favorably, in an instance of the complex. In Examples 2 and 3, it was shown that vaporization properties and thermal stability that were sufficient for deposition were possessed as in Example 1 except that there was seen a drop of around 20° C. in melting point by the introduction of an ethyl group.

Deposition Test:

Next, deposition tests of a platinum thin film were performed by a CVD method using platinum complexes manufactured in Examples 1 to 5 as raw compounds.

Figure 2:
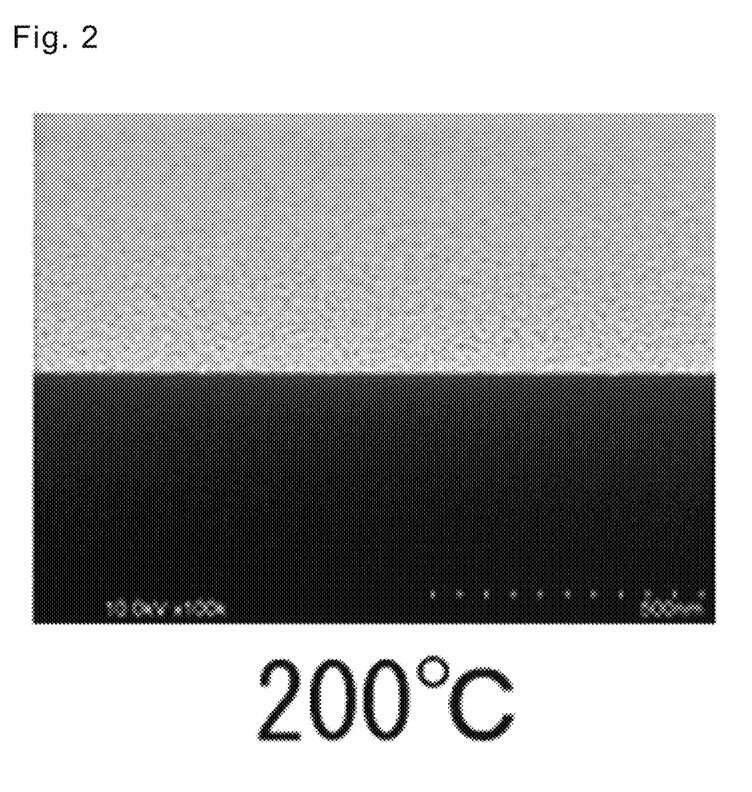
FIG. 2 shows a cross-sectional photograph of a platinum thin film in the first embodiment.

A platinum thin film was deposited on a silicon substrate (15 mm×15 mm). A thermal CVD apparatus of a hot wall type was used as a deposition apparatus. A reaction gas (hydrogen) was flown at a constant flow rate using a mass flow controller. Deposition conditions are as follows. Results are shown in Table 1. Further, there is shown in FIG. 2 a SEM-observed photograph of a platinum thin film that was formed using the complex in Example 1.

Substrate: Si
Film deposition temperature: 200° C.
Sample temperature: 70° C.
Deposition pressure: 5 torr
Flow rate of reaction gas (hydrogen): 10 sccm
Film deposition time: 10 minutes As the results of the above deposition tests, a platinum thin film was able to be deposited and the formed thin film had a flat and uniform surface in all cases where any complex in Examples 1 to 5 was used as a raw material. Film thickness and specific resistance were measured for the platinum thin film that was formed in Example 1, and the Pt film had a sufficient thickness of 8.5 nm and a specific resistance of 174.4 μΩ·cm. Further, the formation of a platinum thin film having a smooth and uniform surface was confirmed also by the SEM photograph in FIG. 2.

Second Embodiment

In the present embodiment, deposition tests onto respective Si substrates in the first embodiment were performed at deposition temperatures of 100° C. and 150° C. to evaluate low temperature deposition properties. Other deposition conditions were the same as the conditions in the first embodiment. Results are shown in Table below. The deposition results in the first embodiment are shown together in the Table below. Further, a SEM-observed result of the formed platinum thin film is shown in FIG. 3.

TABLE 1

| Film deposition temperature (° C.) | Pt film thickness (nm) | Specific resistance (μΩ · cm) |
| --- | --- | --- |
| 100 | 4.5 | 50.9 |
| 150 | 3.5 | 34.0 |
| 200 | 8.5 | 174.4 |

Figure 3:
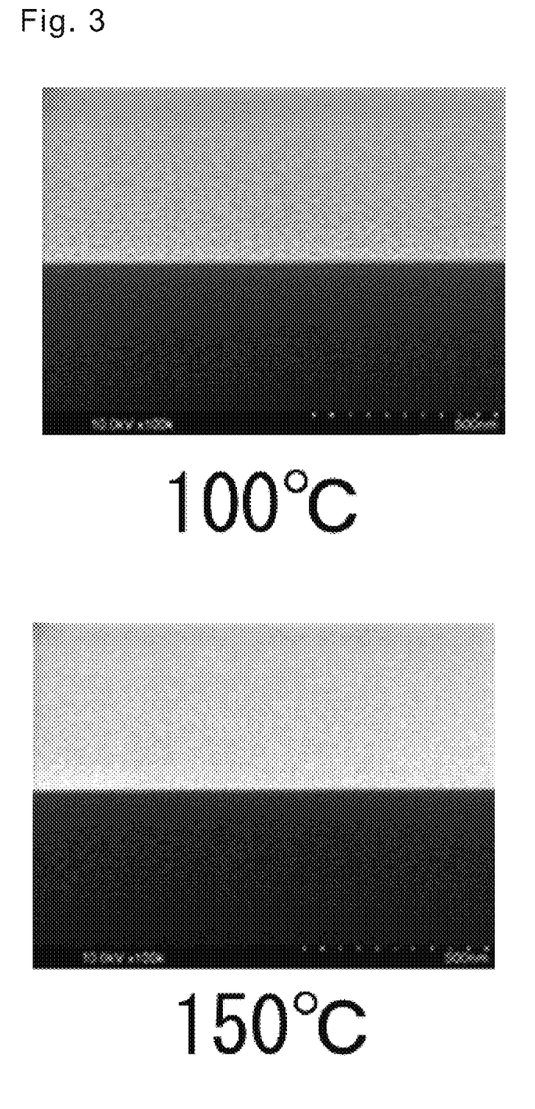
FIG. 3 shows a cross-sectional photograph of a platinum thin film in a second embodiment.

From the SEM photograph in FIG. 3, the platinum thin films that were formed at 100° C. and 150° C. as deposition temperatures also had a flat and uniform surface. Further, the Pt thin films that were formed at 100° C. and 150° C. as deposition temperatures had a moderate film thickness and low specific resistance, from the above Table.

Third Embodiment

In the present embodiment, dimethyl(N,N,N',N'-tetramethylethylenediamine)platinum was used in Comparative Example and vaporization properties and deposition properties were compared with Example 1.

Reduced Pressure TG Measurement (Vaporization Properties):

A platinum complex sample (5 mg) was heated and analyzed with TG-DTA2000SA manufactured by BRUKER Corporation in a measurement temperature range of room temperature to 450° C. at temperature rising rate of 5° C./min and pressure of 5 torr under a nitrogen atmosphere. Results are shown in FIG. 4.

Figure 4:
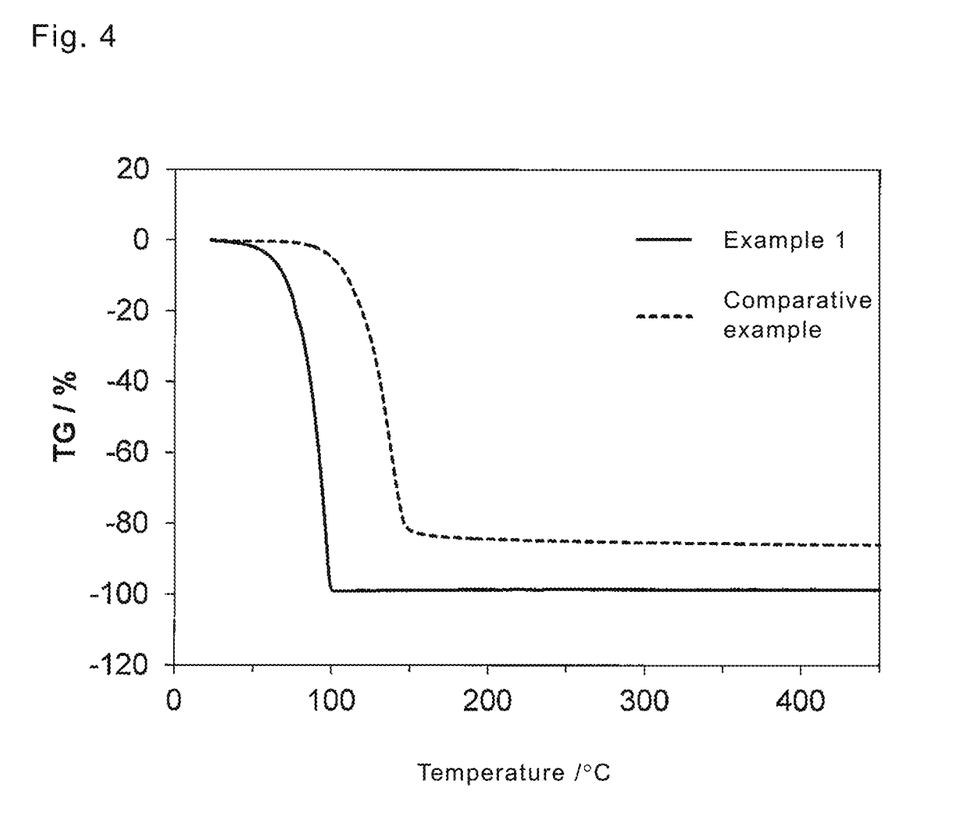
FIG. 4 shows a TG curve of a platinum complex in a third embodiment.

As the result of the TG measurement, from FIG. 4, the complex having aminoalkene in Example 1 was totally vaporized without generating residue but the complex having diamine in Comparative Example generated about 15% residue. It is considered that the diamine ligand had a lower vapor pressure and thermal decomposition was generated before the complex was totally vaporized in the process of temperature rising.

Deposition Test:

Platinum complexes in Examples and Comparative Examples were used as raw materials for chemical deposition to form a Pt thin film on respective substrates Si at 200° C. in deposition temperature. Sample temperatures were set to be 40° C. in Comparative Example 1 and 110° C. in Comparative Example 2. Other deposition conditions were set to be the same as the conditions in the first embodiment.

As the results of the deposition tests, a platinum thin film was formed even at 200° C. in film deposition temperature in the case of the complex in Example 1 but, in contrast, a thin film was not able to be formed in the case of the complex in Comparative Examples because the decomposition of compounds was generated in vaporization of samples.

From the above, it was confirmed that the complex in Example 1 had both vaporization properties and deposition properties suitable for the formation of a platinum thin film.

INDUSTRIAL APPLICABILITY

The present inventive raw material has high vapor pressure to make possible the formation of a highly accurate platinum thin film at low temperature and also has moderate thermal stability to exert excellent handling properties. Consequently, the raw material is useful for the deposition onto a steric structure and can be applied to a stereoscopic electrode having a three-dimensional structure of a field-effect transistor (FET), and the like.

The invention claimed is:

1. A raw material for chemical deposition for manufacturing a platinum thin film or a platinum compound thin film by a chemical deposition method, the raw material comprising
   an organoplatinum compound in which an alkenyl amine and alkyl anions that are coordinated to a divalent platinum as shown by a formula below,

[Chemical Formula 1]

wherein n is 1 or more and 5 or less; each of $R_1$ to $R_5$ represents any one of a hydrogen atom, an alkyl group, an alkenyl group, an alkynyl group, an amino group, an imino group, a cyano group and an isocyano group, and each has a carbon number of not more than 4; and each of $R_6$ and $R_7$ represents an alkyl group having a carbon number of 1 or more and 3 or less.

2. The raw material for chemical deposition according to claim 1, wherein n is 2 or 3, and the raw material comprises any of organoplatinum compounds shown by formulae below,

[Chemical Formula 2]

wherein each of $R_1$ to $R_5$ represents any one of a hydrogen atom, an alkyl group, an alkenyl group, an alkynyl group, an amino group, an imino group, a cyano group and an isocyano group, and each has a carbon number of 4 or less; and each of $R_6$ and $R_7$ represents an alkyl group having a carbon number of 1 or more and 3 or less.

3. The raw material for chemical deposition according to claim 2, wherein each of $R_1$ to $R_5$ represents any one of a hydrogen atom, a methyl group, an ethyl group and a propyl group.

4. The raw material for chemical deposition according to claim 2, wherein each of $R_6$ and $R_7$ represents any one of a methyl group, an ethyl group and an n-propyl group.

5. A chemical deposition method of a platinum thin film or a platinum compound thin film, the method comprising: vaporizing a raw material composed of an organoplatinum compound to form a raw material gas, and heating the raw material gas while introducing the raw material gas onto a substrate surface, wherein the raw material for chemical deposition defined in claim 2 is used as the raw material.

6. The raw material for chemical deposition according to claim 1 wherein each of $R_1$ to $R_5$ represents any one of a hydrogen atom, a methyl group, an ethyl group and a propyl group.

7. The raw material for chemical deposition according to claim 6, wherein each of $R_6$ and $R_7$ represents any one of a methyl group, an ethyl group and an n-propyl group.

8. A chemical deposition method of a platinum thin film or a platinum compound thin film, the method comprising: vaporizing a raw material composed of an organoplatinum compound to form a raw material gas, and heating the raw material gas while introducing the raw material gas onto a substrate surface, wherein the raw material for chemical deposition defined in claim 6 is used as the raw material.

9. The raw material for chemical deposition according to claim 1 wherein each of $R_6$ and $R_7$ represents any one of a methyl group, an ethyl group and an n-propyl group.

10. A chemical deposition method of a platinum thin film or a platinum compound thin film, the method comprising: vaporizing a raw material composed of an organoplatinum compound to form a raw material gas, and heating the raw material gas while introducing the raw material gas onto a substrate surface, wherein the raw material for chemical deposition defined in claim 9 is used as the raw material.

11. A chemical deposition method of a platinum thin film or a platinum compound thin film, the method comprising: vaporizing a raw material composed of an organoplatinum compound to form a raw material gas, and heating the raw material gas while introducing the raw material gas onto a substrate surface, wherein the raw material for chemical deposition defined in claim 1 is used as the raw material.

\* \* \* \* \*